(12) United States Patent
Mundt et al.

(10) Patent No.: US 8,698,037 B2
(45) Date of Patent: Apr. 15, 2014

(54) METHODS OF AND APPARATUSES FOR MAINTENANCE, DIAGNOSIS, AND OPTIMIZATION OF PROCESSES

(75) Inventors: Randall S. Mundt, Pleasanton, CA (US); Paul Douglas MacDonald, Tracy, CA (US); Andrew Beers, Liberty Hill, TX (US); Mason L. Freed, Pleasant Hill, CA (US); Costas J. Spanos, Lafayette, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 164 days.

(21) Appl. No.: 13/159,266

(22) Filed: Jun. 13, 2011

(65) Prior Publication Data

US 2011/0240610 A1    Oct. 6, 2011

Related U.S. Application Data

(62) Division of application No. 11/281,238, filed on Nov. 16, 2005, now Pat. No. 7,960,670.

(60) Provisional application No. 60/722,554, filed on Sep. 30, 2005.

(51) Int. Cl.
   *B23K 10/00*    (2006.01)

(52) U.S. Cl.
   USPC .............. 219/121.54; 219/121.43; 219/497; 219/1; 156/345.27; 156/345.28

(58) Field of Classification Search
   CPC ........................................... H05H 1/36
   USPC .............. 219/121.54, 121.57, 121.43; 156/345.24, 345.25, 345.27, 345.28; 118/723 R
   See application file for complete search history.

(56) References Cited

U.S. PATENT DOCUMENTS

| | | |
|---|---|---|
| 4,438,394 A | 3/1984 | Ekdahl |
| 4,458,202 A | 7/1984 | Nefedov et al. |
| 5,371,336 A | 12/1994 | Albert et al. |

(Continued)

FOREIGN PATENT DOCUMENTS

| | | |
|---|---|---|
| DE | 10314150 | 10/2004 |
| EP | 1014437 | 6/2000 |

(Continued)

OTHER PUBLICATIONS

Wayne Renken et al., U.S. Appl. No. 60/430,858, filed Dec. 3, 2002.

(Continued)

*Primary Examiner* — Mark Paschall
(74) *Attorney, Agent, or Firm* — Joshua D. Isenberg; JDI Patent

(57) ABSTRACT

A sensor apparatus for measuring a plasma process parameter for processing a workpiece. The sensor apparatus includes a base, an information processor supported on or in the base, and at least one sensor supported on or in the base. The at least one sensor includes at least one sensing element configured for measuring an electrical property of a plasma and may include a transducer coupled to the at least one sensing element. The transducer can be configured to receive a signal from the sensing element and convert the signal into a second signal for input to the information processor.

7 Claims, 10 Drawing Sheets

(56) References Cited

U.S. PATENT DOCUMENTS

| | | |
|---|---|---|
| 5,444,637 A | 8/1995 | Smesny et al. |
| 5,810,936 A | 9/1998 | Leung et al. |
| 5,971,591 A * | 10/1999 | Vona et al. ............ 700/220 |
| 5,989,349 A | 11/1999 | Ke et al. |
| 6,140,833 A | 10/2000 | Flientner et al. |
| 6,244,121 B1 | 6/2001 | Hunter |
| 6,553,277 B1 | 4/2003 | Yagisawa et al. |
| 6,691,068 B1 | 2/2004 | Freed et al. |
| 6,830,650 B2 | 12/2004 | Roche et al. |
| 6,882,143 B2 | 4/2005 | Clymer et al. |
| 6,902,646 B2 | 6/2005 | Mahoney et al. |
| 7,504,643 B2 | 3/2009 | Freriks et al. |
| 7,514,936 B2 * | 4/2009 | Anwar et al. ............ 324/536 |
| 7,722,778 B2 | 5/2010 | Fischer et al. |
| 7,960,670 B2 | 6/2011 | Mundt et al. |
| 2001/0053265 A1 * | 12/2001 | Yamashita et al. ............ 385/48 |
| 2002/0030038 A1 * | 3/2002 | Bollinger et al. ........ 219/121.54 |
| 2003/0155080 A1 | 8/2003 | Chen et al. |
| 2004/0007326 A1 | 1/2004 | Roche et al. |
| 2005/0011611 A1 | 1/2005 | Mahoney et al. |
| 2005/0034811 A1 | 2/2005 | Mahoney et al. |
| 2005/0034812 A1 | 2/2005 | Roche et al. |
| 2005/0115673 A1 | 6/2005 | Samukawa |
| 2005/0151544 A1 | 7/2005 | Mahoney et al. |
| 2005/0194094 A1 | 9/2005 | Yasaka |
| 2005/0217796 A1 | 10/2005 | Carter et al. |
| 2005/0284570 A1 | 12/2005 | Doran et al. |
| 2006/0043063 A1 | 3/2006 | Mahoney et al. |
| 2009/0053016 A1 | 2/2009 | van der Meulen |
| 2009/0151871 A1 * | 6/2009 | Pease et al. ............ 156/345.28 |

FOREIGN PATENT DOCUMENTS

| | | |
|---|---|---|
| JP | H763833 | 3/1995 |
| JP | 2003243370 | 8/2003 |
| JP | 2003282546 | 10/2003 |
| JP | 2003318115 | 11/2003 |
| WO | 200099063 | 11/2004 |

OTHER PUBLICATIONS

Notice of Allowance mailed Feb. 3, 2011 in U.S. Appl. No. 11/281,238, filed Nov. 16, 2005.

Non-final Office Action mailed Aug. 16, 2010 in U.S. Appl. No. 11/281,238, filed Nov. 16, 2005.

Final Office Action mailed May 26, 2010 in U.S. Appl. No 11/281,238, filed Nov. 16, 2005.

Non-final Office Action mailed Nov. 10, 2009 in U.S. Appl. No. 11/281,238, filed Nov. 16, 2005.

Non-final Office Action mailed Apr. 28, 2009 in U.S. Appl. No. 11/281,238, filed Nov. 16, 2005.

Randall S. Mundt et al., U.S. Appl. No. 60/722,554, filed Sep. 30, 2005.

Japanese Office Action issued date on May 8, 2012 for Japanese Application No. 2008-533652, entitled "Methods of and Apparatuses for Measuring Electrical Parameters of a Plasma Process".

* cited by examiner

METHODS OF AND APPARATUSES FOR MAINTENANCE, DIAGNOSIS, AND OPTIMIZATION OF PROCESSES

CROSS-REFERENCE

The present application is a divisional application of U.S. patent application Ser. No. 11/281,238 to Randall S. MUNDT, Paul D. MACDONALD, Andrew BEERS, Mason L. FREED, and Costas J. SPANOS filed Nov. 16, 2005, entitled METHODS OF AND APPARATUSES FOR MEASURING ELECTRICAL PARAMETERS OF A PLASMA PROCESS, the entire contents of which are incorporated herein by reference.

Application Ser. No. 11/281,238 is a nonprovisional of U.S. Patent Application Ser. No. 60/722,554, filed 30 Sep. 2005. The present application is likewise a nonprovisional application that claims the priority benefit of U.S. Patent Application Ser. No. 60/722,554, filed 30 Sep. 2005.

The present application is related to U.S. Patent Application Ser. No. 60/722,554, filed 30 Sep. 2005; U.S. Pat. No. 6,691,068, filed 22 Aug. 2000; U.S. Pat. No. 6,542,835, filed 22 Mar. 2001; U.S. Patent Application 60/285,439, filed 19 Apr. 2001; and U.S. Patent Application 60/677,545, filed 3 May 2005; all of these patents are incorporated herein, in their entirety, by this reference.

TECHNICAL FIELD

This invention relates to methods of and apparatuses for measuring electrical parameters within a plasma processing system. More specifically, this invention relates to plasma processes used to treat and/or modify the surfaces of work pieces such as semiconductor wafers, flat panel display substrates, and lithography masks.

BACKGROUND

Plasma processes are frequently used to modify or treat the surfaces of workpieces such as semiconductor wafers, flat-panel display substrates, and lithography masks. Conditions within a plasma process are designed to produce a complex mixture of ions, reactive chemical species (free radicals), and energetic neutral species. The interaction of these materials then produces the desired effect on the surfaces of work pieces. For example, plasma processes are used to etch materials from the surfaces of semiconductor wafers so as to form complex electrical elements and circuits. The conditions within the plasma process are carefully controlled to produce the desired etch directionality and selectivities.

The surface modifications produced by a specific plasma are sensitive to a number of basic parameters within the plasma. These parameters include such variables as: chemical concentrations (partial pressures), temperatures (both surface and gas phase), and electrical parameters (ion fluxes, ion energy distribution functions). A number of these parameters (e.g. gas concentrations and pressure) can generally be easily controlled using external actuators such as Mass Flow Controllers (MFCs) and servo driven throttle valves. Other important parameters (e.g. temperatures and free radical concentrations) can often be observed or measured via sensor systems (e.g. thermocouples and Optical Emission Spectrometers (OES)) installed on the process tool. A last set of important parameters such as ion fluxes and ion energies are more difficult to either directly control or monitor.

A prime reason that these important electrical parameters are difficult to measure in a plasma process chamber is that the parameters result from a complex, nonlinear interaction between the applied driving force (RF power) and the local physical state in the process chamber. For example, a localized increase in ion concentrations can lead to locally increased RF power flows, which in turn leads to higher ion concentrations. This interaction and feedback can lead to highly non-uniform and unstable plasma conditions. It is typically impossible to adequately characterize the plasma state with a single, localized measurement.

Plasma electrical parameters have been measured with a wide variety of sensors and methods. These include: Biased probes (voltage or frequency swept), Wall probes (swept frequency), Optical emission (actinometry and Doppler), Microwave absorption, and Passive electrodes (SPORT, CHARM).

Each of these sensor types and methodologies suffer from one of more significant flaws which prevent their routine use in plasma process monitoring. Some of the most common flaws are that the sensors are either unacceptably intrusive (they excessively modify or interact with the local plasma state) or they provide an aggregate measurement lacking spatial resolution. Another deficiency found in some of the currently available techniques is their high cost due to the complexity and sensitivity of the instrumentation needed.

There is a need for improved methods and apparatuses for measuring plasma process parameters such those used for plasma processing substrates such as, but not limited to, semiconductor substrates, flat panel display substrates, and lithography mask substrates. More particularly, there is a need for improved methods and apparatuses for measuring process parameters such as plasma density, plasma uniformity, ion energy distributions, electron energy distributions, ion fluxes, and ion energies.

SUMMARY

This invention seeks to provide methods and apparatus that can overcome one or more problems related to measuring electrical properties of a plasma for processing workpieces. One aspect of the present invention includes methods of measuring electrical properties of a plasma using a sensor apparatus. The measurements include data for applications such as monitoring, controlling, and optimizing processes and process tools. Another aspect of the present invention includes a sensor apparatus for measuring electrical properties of a plasma for processing workpieces.

It is to be understood that the invention is not limited in its application to the details of construction and to the arrangements of the components set forth in the following description or illustrated in the drawings. The invention is capable of other embodiments and of being practiced and carried out in various ways. In addition, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out aspects of the present invention. It is important, therefore, that the claims be regarded as including such equivalent constructions insofar as they do not depart from the spirit and scope of the present invention.

The above and still further features and advantages of the present invention will become apparent upon consideration of the following detailed descriptions of specific embodiments thereof, especially when taken in conjunction with the accompanying drawings.

Figure 1:
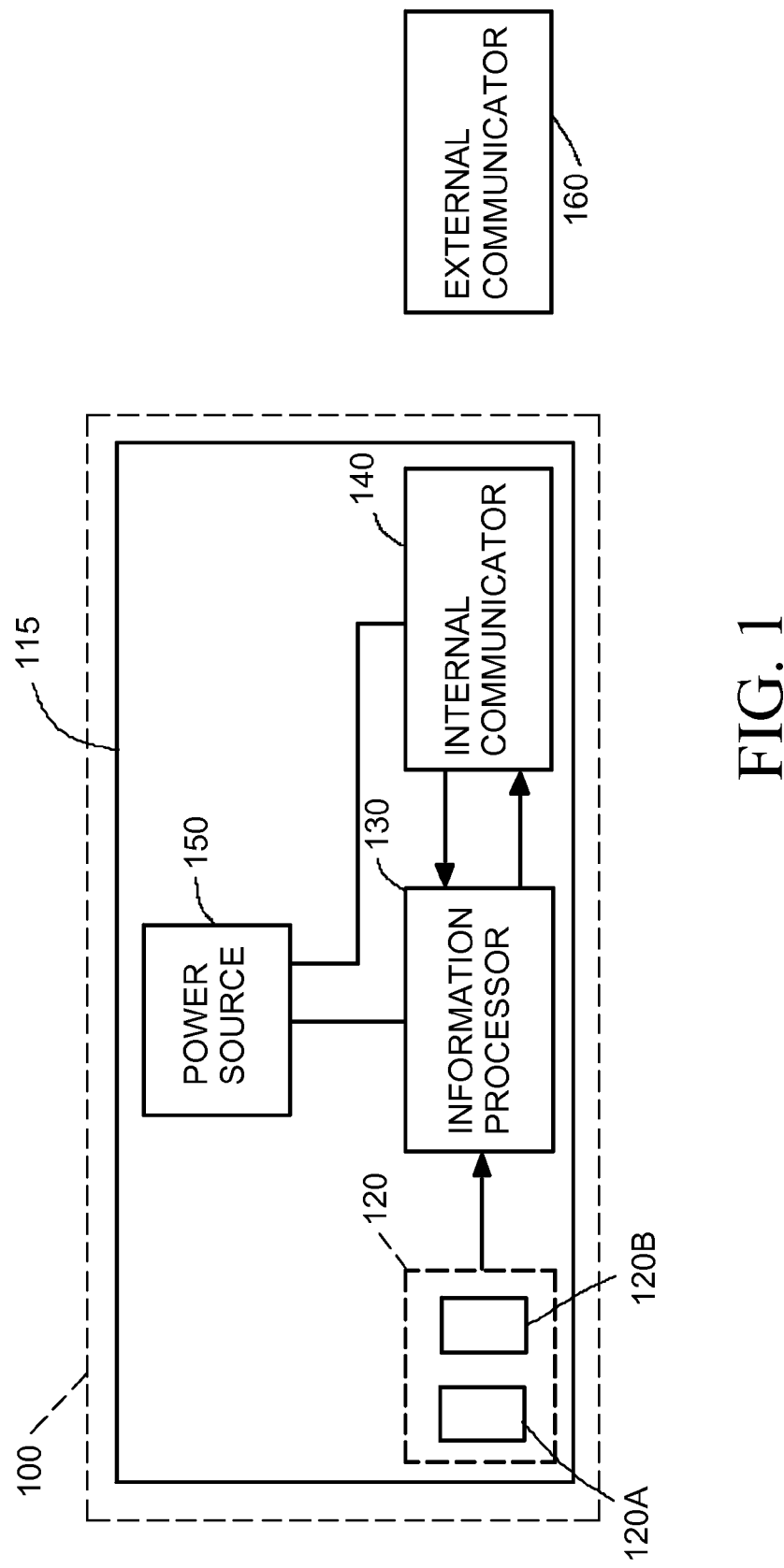
FIG. 1 is a box diagram of a sensor apparatus according to an embodiment of the present invention and an external communicator.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DESCRIPTION

The present invention pertains to measuring process parameters for processing a workpiece using a plasma process. The operation of embodiments of the present invention will be discussed below, primarily, in the context of processing semiconductor wafers, lithography mask substrates, or flat panel display substrates. However, it is to be understood that embodiments in accordance with the present invention may be used for measuring plasma process characteristics for essentially any plasma-processing step involving a workpiece subjected to possible temporal and/or spatial variations in plasma process conditions and/or process conditions that occur during plasma processing.

In the following description of the figures, identical reference numerals have been used when designating substantially identical elements or steps that are common to the figures.

Reference is now made to FIG. 1 wherein there is shown a block diagram for a sensor apparatus 100 according to one embodiment of the present invention. Sensor apparatus 100 is configured for measuring a process parameter for plasma processing a workpiece. Sensor apparatus 100 is further configured for transmitting or receiving information. For illustration purposes, FIG. 1 also shows an external communicator 160 which may be used for communication with embodiments of the present invention.

Sensor apparatus 100 includes a base 115, a sensor 120, preferably a plurality of sensors 120, an information processor 130, an internal communicator 140, and a power source 150. Sensors 120, information processor 130, internal communicator 140, and power source 150 are supported on or in base 115. Sensors 120 are connected with information processor 130 so as to allow signals generated by sensors 120 to be provided as input to information processor 130. Information processor 130 is connected with internal communicator 140 so as to allow information and data from information processor 130 to be transferred to internal communicator 140. In preferred embodiments, information processor 130 is connected with internal communicator 140 so as to allow bi-directional information transfer between information processor 130 and internal communicator 140.

Sensors 120 may include discrete sensor devices attached to base 115. Alternatively, sensors 120 may be fabricated as part of base 115. In other words, base 115 may be processed to fabricate sensors 120 as an integrated part of base 115. Sensors 120 are designed to provide an electrical signal proportional to one or more plasma process parameters representative of the plasma process and process tool. Examples of process parameters of importance for applications such as semiconductor processing and flatpanel display processing include radio frequency (RF) field, plasma potential, ion flux, electromagnetic flux such as light, and any process parameter that is affected by the plasma used for the process. Examples of typical sensor types include: defined area probes for measuring plasma potential and measuring ion flux; Van der Pauw crosses for measuring etch rate; isolated field transistors for measuring plasma potential; and current loops for measuring ion flux and measuring RF field. The numbers and types of sensors are selected based upon the specific application and process requirements.

In preferred embodiments of the present invention, sensor 120 comprises a sensing element 120A and a transducer 120B. Sensing element 120A is configured so as to be responsive to the process parameter being measured so that sensing element 120A produces a signal proportional to a plasma process parameter, such as a signal proportional to the magnitude of the process parameter. Transducer 1208 is connected with sensing element 120A to receive the signal from sensing element 120A. Transducer 1208 converts the signal from sensing element 120A into a signal for which information processor 130 is configured to receive.

In more preferred embodiments of the present invention, sensing element 120A and transducer 1208 are configured so as to provide improved operation of the sensor. The sensing element is configured to more effectively accommodate the process parameter being measured and the transducer is configured so as to convert the signal from the sensing element to accommodate the signal measurement requirements for the information processor. For some embodiments of the present invention, sensor apparatus 100 is configured for substantially non-intrusive measurement of important plasma parameters used for processing workpieces. For such embodiments, sensor 120 is configured so that sensing element 120A does not require direct electrical connections to the plasma.

For some applications for embodiments of the present invention, it is necessary or desirable to convert the output of the sensing element into a form that is more easily or more accurately measurable. As an example, the output of a particular sensor type (e.g. capacitive current) may be an alternating RF voltage while the measurement circuitry is optimized for measuring a DC voltage. In these cases, one embodiment of the present invention includes a transducer used to transform the raw output of a sensing element into a more readily measured form that can be accommodated by the information processor. For some embodiments of the present invention, the transducer can also be used to scale the sensor output into a suitable measurement range. The selection of an appropriate transducer circuit is dependent upon both the sensing element being used as well as the measurement circuitry. In some embodiments of the present invention, the transducer circuit can be integrated into the sensor. For some embodiments of the present invention, the sensing element and the transduction method and components are treated as independent elements that are optimized for a particular process parameter measurement.

In one embodiment of the present invention, sensor apparatus 100 includes a plurality of sensors 120 configured for measuring RF current or RF voltage; an example of a suitable sensor is a capacitive sensor. More specifically, sensors 120 include sensing elements 120A comprising capacitive elements. For this embodiment, sensors 120 are configured as part of sensor apparatus 100 so as to be in series with radio frequency current flow from the plasma, through the plasma sheath, and into base 115. The capacitive element is designed to have a low relative reactance so as to produce a minimal perturbation of the plasma. More specifically, preferred embodiments of a capacitive sensor are configured so as to minimize a local increased impedance for the plasma. As an option for another embodiment of the present invention, sensor apparatus 100 includes one or more differential capacitive sensors formed by coupling two adjacent capacitive elements so as to extrapolate local radio frequency voltages.

In another embodiment of the present invention, sensor apparatus 100 includes a plurality of sensors 120 configured for measuring RF currents; an example of a suitable sensor is an inductive sensor. More specifically, sensors 120 include sensing elements 120A comprising an inductor coil such as a closed loop of magnetically permeable material and a second electrically conductive coil wrapped around the magnetically permeable loop in a toroidal fashion as a sense coil. In other words, one embodiment of the present invention includes a toroidal coil with a magnetically permeable material core. The loop of magnetically permeable material is orientated substantially parallel to the surface of base 115 such that radio frequency current from the plasma passes through the loop. The radio frequency current induces an alternating magnetic field within the closed loop of magnetically permeable material. The alternating magnetic field induces a current flow within the sense coil. The current in the second electrically conductive loop is applied to transducer 120B.

In another embodiment of the present invention, sensor apparatus 100 includes a plurality of sensors 120 configured for measuring electrostatic charge; in other words, electrostatic charge sensors. More specifically, sensors 120 include sensing elements 120A responsive to electrostatic charge. In one configuration, sensing elements 120A includes a layer of an electrical conductor such as a layer of metal and a semiconductor such as a semiconductor layer. The electrical conductor is proximate to the surface of the semiconductor and electrically isolated from the semiconductor. As an option for one embodiment, the electrical conductor and the semiconductor are separated by a layer of an electrically insulating material. In this configuration, charge collected on the electrical conductor can moderate the conductivity of the semiconductor. Transducer 120B is configured so as to measure the conductivity of the semiconductor. In operation, charge is collected on the electrical conductor as a result of exposure to the plasma for which process parameters are being measured. The conductivity of the semiconductor is measured in order to determine the magnitude of the charge collected. As an option for some embodiments of the present invention, differential measurements can be made for semiconducting layers having different thicknesses of dielectric between the electrical conductor and the semiconductor so as to produce an estimation of the charge and potential.

In still another embodiment of the present invention, sensor apparatus 100 includes a plurality of sensors 120 configured for measuring optical emission from the plasma; in other words, optical emission sensors. More specifically, sensors 120 include sensing elements 120A responsive to optical emission intensity. Sensing elements 120A include photosensitive material that undergoes a change in resistance in response to optical emissions from the plasma. The changes in the resistance are correlated to plasma properties such as local plasma densities and local ion density. As an option for some embodiments of the present invention, sensing elements 120A further include an optical filter for filtering light from the plasma so as to selectively permit or inhibit various wavelengths of interest. Optionally, the properties of the photosensitive material may be selected so that the wavelength response of the photosensitive material extends beyond the visible spectrum.

Preferred embodiments of the present invention use one or more of the following transducer circuits in transducer 120B at or near each sensor position on sensor apparatus 100: diode rectification, power detection, optical transduction, and resistance measurement. For the diode rectification circuit, radio frequency voltages or radio frequency current induced in a capacitive or inductive sensing element, as disclosed above, are connected through a diode to a high impedance load, such as a high resistance load, to provide a measure of the peak to peak radio frequency potential. Alternatively, the radio frequency voltages or radio frequency current induced in a capacitive or an inductive sensing element is connected to a low impedance load to provide a measure of the local radio frequency current. In a further embodiment, identical sensor elements are connected to impedances of different values so as to be capable of measuring nonlinear plasma current-voltage characteristics. As an option for another embodiment of the present invention, signals from the sensing elements may be applied to a complex load having resistive, inductive, and capacitive properties so as to be capable of making frequency sensitive measurements.

For the power detection circuit, transducer 120B includes a resistor and a temperature measuring device coupled so that the temperature measuring device, such as a thermistor, measures the temperature of the resistor. Radio frequency current (either RF or direct current) induced in sensing element 120A is coupled to the resistor. The currents cause heating of the resistor as determined by the product of the current squared multiplied by the resistance of the resistor. The temperature rise of the resistive element is then detected using the temperature measuring device. Preferably, the temperature measuring device is electrically isolated from the resistor.

Embodiments of the present invention for which transducer 120B comprises an optical transduction circuit, the transduction circuit preferably includes a light emitting diode. The light emitting diode is connected with sensing element 120A so as to receive current signals from sensing element 120A. The intensity of the light emitted by the light emitting diode is proportional to the current received by the light emitting diode. Transducer 120B further includes a light detecting device such as a photoresistor or a photodiode. The light detecting device is arranged so as to be capable of measuring light produced by the light emitting diode so as to produce a current proportional to the light produced by the light emitting diode. The current from the light measuring device is applied to the information processor as described above.

In some embodiments of the present invention that use sensing elements 120A configured to provide an impedance proportional to the property being measured, transducer 120B is incorporated in an impedance measuring circuit. In a preferred embodiment for measurements on a large number of sensors, transducer 1208 is configured as a node in a crosspoint network substantially as described in commonly owned U.S. Pat. No. 6,542,835 and U.S. Pat. No. 6,789,034. The contents of U.S. Pat. No. 6,542,835 and U.S. Pat. No. 6,789,034 are incorporated herein in their entirety by this reference.

In a preferred embodiment of the present invention, sensing element 120A produces an output signal such as current, voltage, and RF current. The output signal from sensing element 120A is coupled to a transducer 1208 where the output signal from sensing element 120A is converted to a change in electrical resistance proportional to the process parameter that is being measured. Transducer 1208 is incorporated as a node in a crosspoint network of resistors. Changes in the resistance produced by transducer 1208 are measured with the crosspoint network of resistors as described in commonly owned U.S. Pat. No. 6,542,835 and U.S. Pat. No. 6,789,034. In a more preferred embodiment, the crosspoint network includes reference resistors of known value. Details of such a crosspoint network are provided in commonly owned U.S. Pat. No. 6,542,835 and U.S. Pat. No. 6,789,034.

The electrical output of sensors 120 may be applied to information processor 130 and digitized therein in a number of ways. In one embodiment of the present invention, the electrical output from sensors 120 comprises direct voltage. Sensor apparatus 100 includes analog multiplexers used to allow data acquisition from a large number of sensors 120 distributed on the surface of base 115. Electrical current flows may be measured by monitoring the voltage developed across a known resistance. In another embodiment, sensor apparatus 100 includes a discrete A/D circuit either integrated into or located in close proximity to sensors 120. In such an embodiment, the measured parameter is transmitted in digital form to electronics module 130.

For sensors which produce a change in capacitance in response to the parameter being measured, the measurements may be obtained by determining the time required to transition between two established voltage states as a result of charging from a known current source or impedance. Alternatively, a capacitive divider circuit formed using a known capacitance may be driven with an alternating voltage of known magnitude and the magnitude of the divided signal used to derive the sensor measurement value.

Power source 150 is connected with information processor 130 so as to provide electric power to information processor 130. Power source 150 is connected with internal communicator 140 so as to provide electric power to internal communicator 140. Embodiments of the present invention may include sensors 120 for which sensors 120 require electric power for operation; for those embodiments, power source 150 is connected with sensors 120 so as to provide electric power to sensors 120. For some embodiments of the present invention, sensing element 120A may require electrical power for operation or transducer 1208 may require electrical power for operation. In alternative embodiments, sensors 120 do not require electric power; consequently, connection with electric power source 150 is unnecessary for such embodiments.

Information processor 130 has information-processing capabilities like those of a computer. Information processor 130 preferably includes information processing devices such as a central processing unit, a microprocessor, an application-specific integrated circuit, and field programmable gate arrays. A preferred embodiment of the present invention comprises an information processor having a microprocessor. There are numerous microprocessors that are suitable for use in embodiments of the present invention. Microchip Technologies, Inc. produces a number of microprocessors that are suitable for embodiments of the present invention. Some of the commercially available microprocessors are capable of signal conditioning and analog to digital conversion of input signals.

Internal communicator 140 is a transmitter capable of transmitting information and data received from information processor 130 to a receiver such as external communicator 160 shown in FIG. 1. Preferably, internal communicator 140 is configured so as to be capable of wirelessly transmitting information to external communicator 160. For embodiments in which information processor 130 and internal communicator 140 are coupled for bi-directional information transfer, it is preferred for internal communicator 140 to be capable of transmitting information to a receiver in addition to receiving information from a transmitter.

Figure 2:
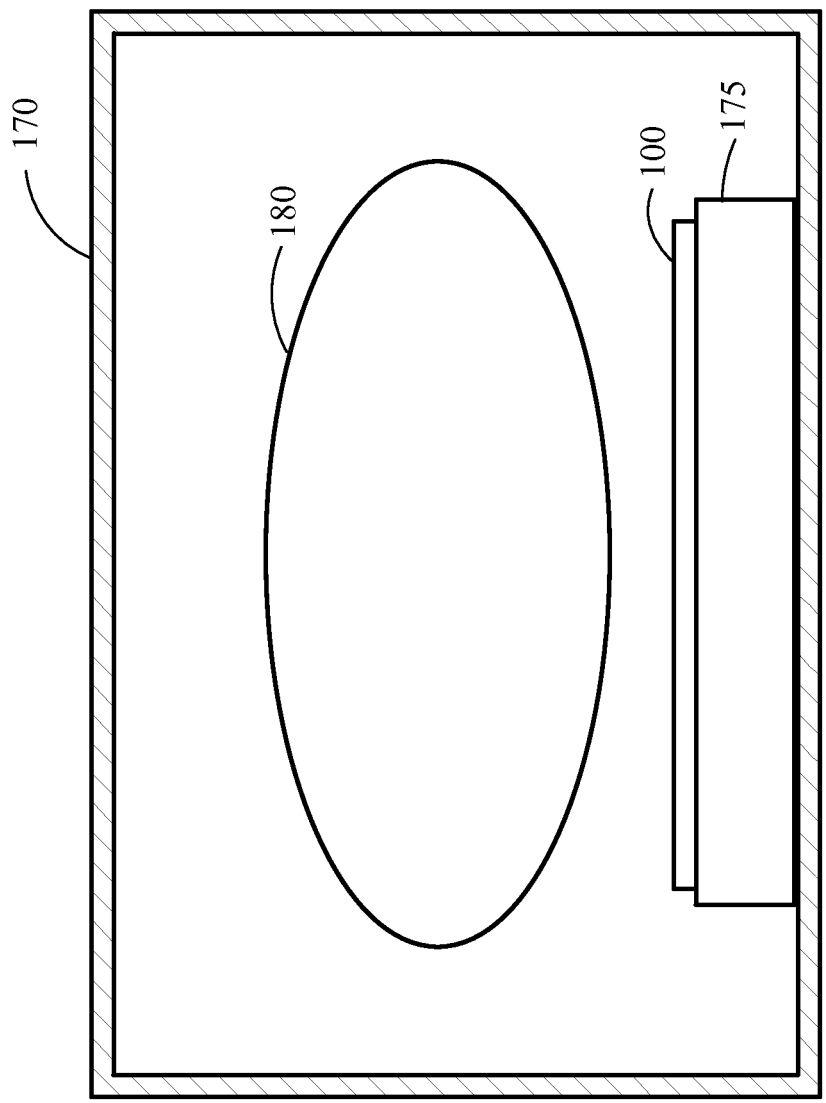
FIG. 2 is a side view diagram of a sensor apparatus according to an embodiment of the present invention used in a plasma process chamber.

Reference is now made to FIG. 2 where there is shown a sensor apparatus 100, according to one embodiment of the present invention in use in a plasma chamber 170. Sensor apparatus 100 is supported on a workpiece holder 175. Sensor apparatus 100 is exposed to plasma 180 so as to make spatial and/or temporal measurements of a process parameter related to plasma 180 for a plasma process. Plasma chamber 170 is substantially the same as the types of plasma chambers typically used for processing workpieces such as semiconductor wafers and flat panel display substrates. Plasma 180 can be generated using typical plasma sources used for processing workpieces. It is typical for plasma chamber 170 to have a robot handler associated with it for loading and unloading workpieces, (robot handler not shown in FIG. 2). For preferred embodiments, sensor apparatus 100 is configured so as to be loaded and unloaded to and from process chamber 170 using the robot handler in essentially the same way that workpieces are loaded and unloaded.

Figure 3:
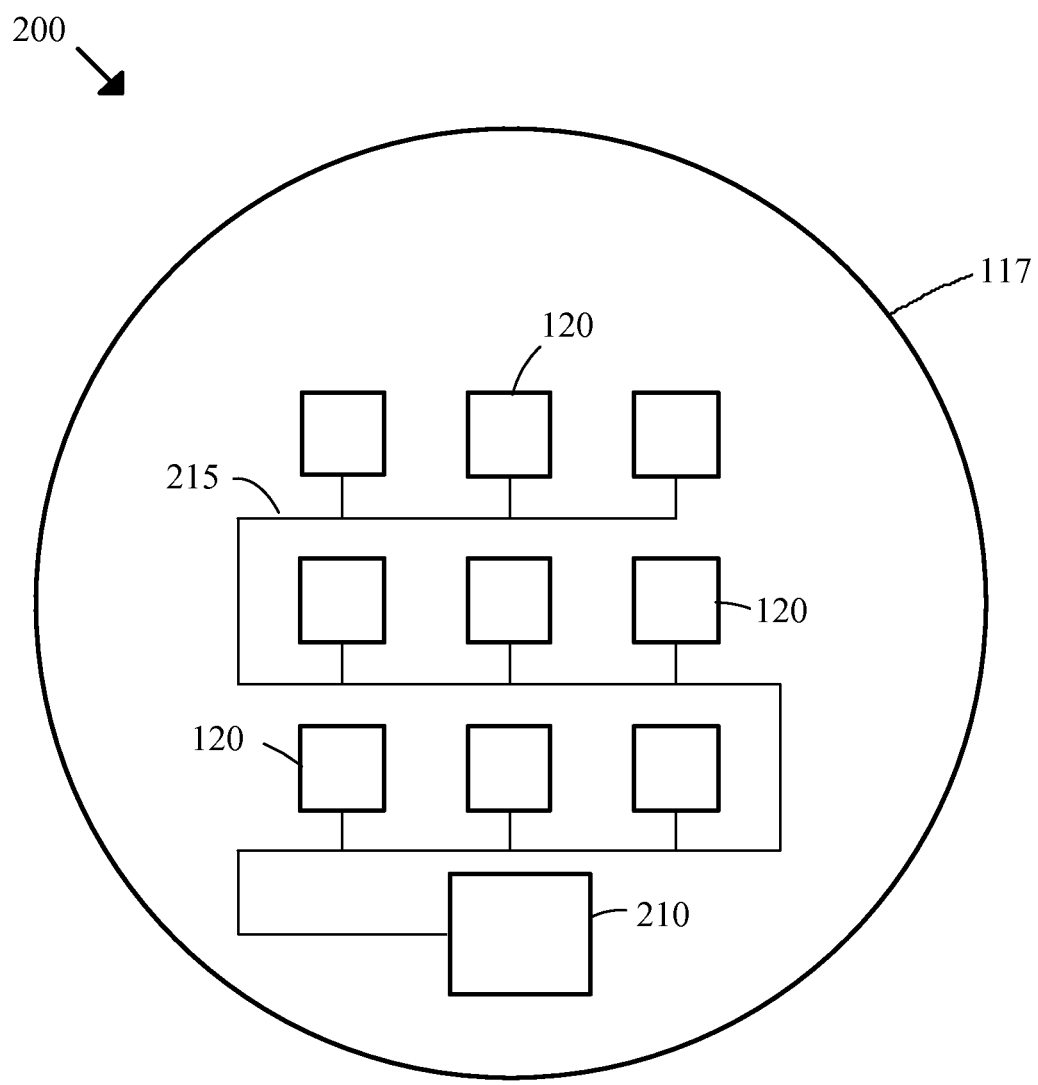
FIG. 3 is a top view diagram of an embodiment of the present invention.

Reference is now made to FIG. 3 where there is shown a top view of a sensor apparatus 200 according to one embodiment of the present invention. Sensor apparatus 200 is configured so as to be capable of measuring parameter data for plasma processing a workpiece. Sensor apparatus 200 includes a base 117, a plurality of sensors 120 such as the nine sensors shown in FIG. 3, an electronics module 210, and metallization lines 215 connecting sensors 120 with electronics module 210. Sensors 120 and electronics module 210 are supported on or in base 117.

Electronics module 210 includes electronic components, preferably contained on a support structure such as a printed circuit board or contained in a housing (printed circuit board and housing not shown in FIG. 3). In a preferred embodiment, electronics module 210 contains an information processor and additional electronic components that may be needed for the operation of the information processor. In general, electronics module 210 may contain an information processor, a power source for the information processor, and an internal communicator. The electronic components of electronics module 210 are substantially the same as those described for the embodiment described in FIG. 1. More specifically, electronics module 210 may also contain components for transmitting and receiving information such as, for example, components for wireless communication. Sensors 120 are connected with the information processor so as to allow signals generated by sensors 120 to be provided as input to the information processor.

Optionally, for some embodiments of the present invention for semiconductor processing applications, base 117 comprises a semiconductor wafer, preferably a substantially whole semiconductor wafer such as a silicon wafer or such as a gallium arsenide wafer. Similarly, for flatpanel display applications, base 117 may comprise a flatpanel display substrate; for lithography mask applications, base 117 may comprise a lithography mask substrate. In preferred embodiments, base 117 is a structure such as a semiconductor wafer, a lithography mask substrate, and a flat panel display substrate. Generally, base 117 is configured so as to substantially mimic the workpiece; more preferably, base 117 comprises the workpiece.

Figure 3A:
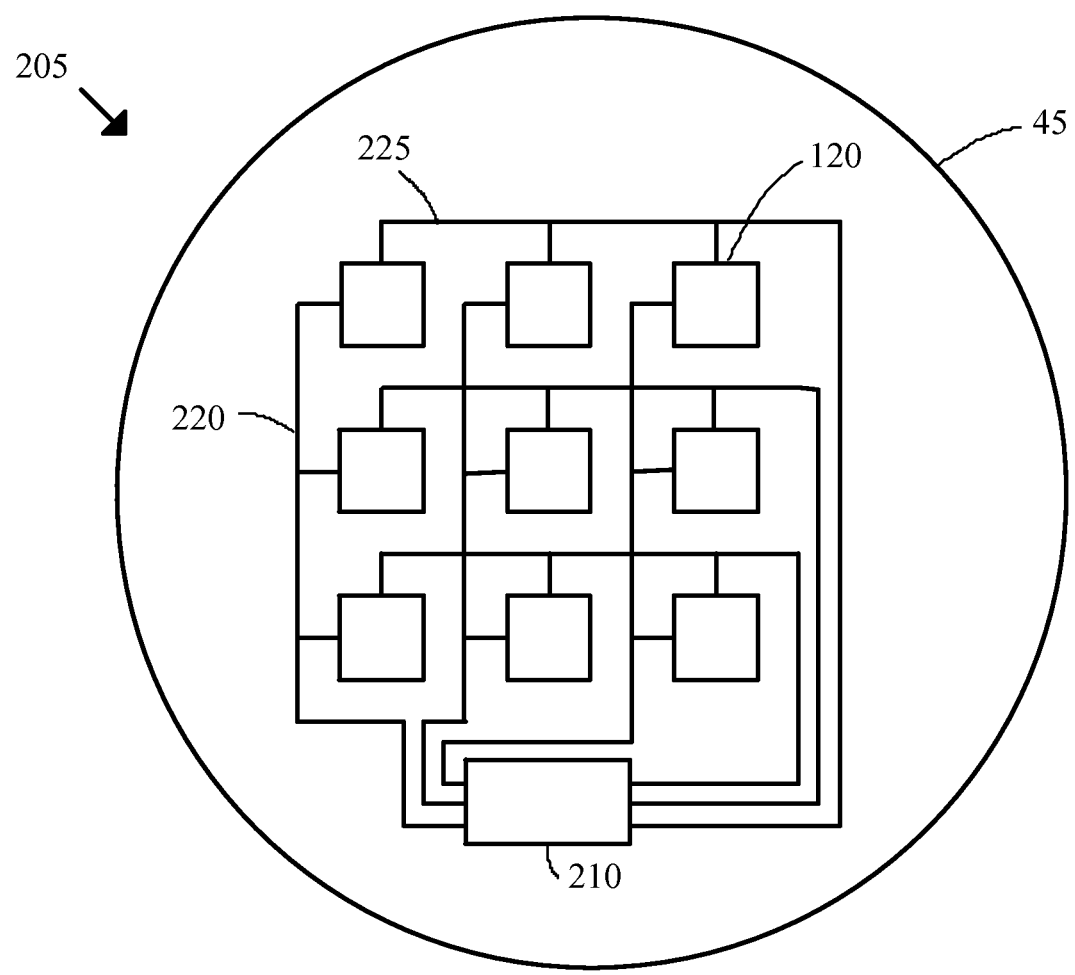
FIG. 3A is a top view diagram of an embodiment of the present invention.

Reference is not made to FIG. 3A where there is shown a top view of another embodiment of the present invention. The embodiment shown in FIG. 3A is essentially the same as that shown in FIG. 3 with the exception that the embodiment in FIG. 3A includes metallization lines 220 and 225 configured so that the sensors are connected in a crosspoint network. More specifically, the transducers for the sensors are connected as nodes in the crosspoint network. Details of a suitable crosspoint network are described in commonly owned U.S. Pat. No. 6,542,835 and U.S. Pat. No. 6,789,034.

Next, examples of preferred methods for fabricating examples of sensing elements and examples of preferred sensing element configurations for embodiments of the present invention will be presented.

Capacitive Sensing Element

Figure 4A:
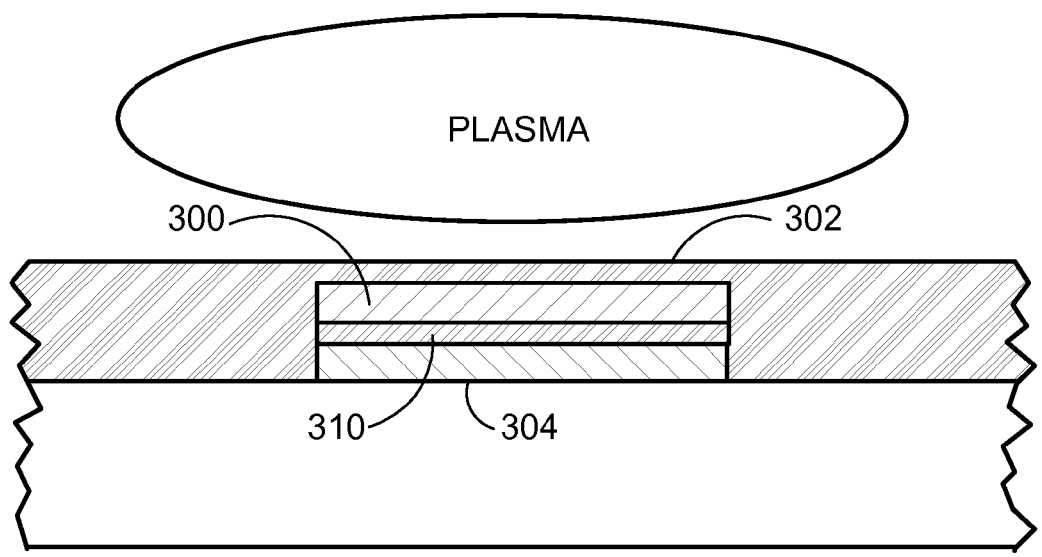
FIG. 4A is a side view of a sensing element according to one embodiment of the present invention.

Reference is now made to FIG. 4A. An example configuration of a capacitive sensing element, according to the present invention, is shown in FIG. 4A in a cross-section side view. The capacitive sensing element includes a planar conductive electrode 300 of known area. The material and surface area of electrode 300 are selected to provide compatibility with the process conditions to be measured. Conductive electrode 300 may either be indirectly exposed to the plasma or, in a preferred embodiment, protected from the plasma by a thin, inert dielectric material 302 as shown in FIG. 4A. An example of a suitable material for dielectric 302 is KAPTON. The sensing element also includes a second planar conductive electrode 304 disposed below electrode 300 and a base 320. Base 320 provides support for electrode 304; base 320 and electrode 304 are coupled so that they form a low impedance contact. Preferably, base 320 comprises a semiconductor wafer. For some embodiments of the present invention, electrode 300 has areas in the range 0.1 $cm^2$ to 10 $cm^2$. Electrode areas between 0.1 $cm^2$ and 5 $cm^2$ are particularly useful. The shape of the electrode may be circular in order to minimize edge effects or elongated so as to measure the parameter of interest at a specific circumference of the base.

The sensing element also includes a dielectric material 310 of known characteristics located between conductive electrode 300 and conductive electrode 304. The thickness and material of dielectric material 310 are selected to minimize the capacitive reactance while providing acceptable voltage breakdown values. A well-characterized and controlled polymeric material such as polyimide, polyester, and polyolypara-xylylene are examples of preferred materials for dielectric material 310. For some embodiments of the present invention, the thickness of the dielectric material is in the range of 1 micrometer to 100 micrometers. More preferably, the thickness of the dielectric ranges from 10 micrometers to 50 micrometers; this range is of particular value.

Figure 4B:
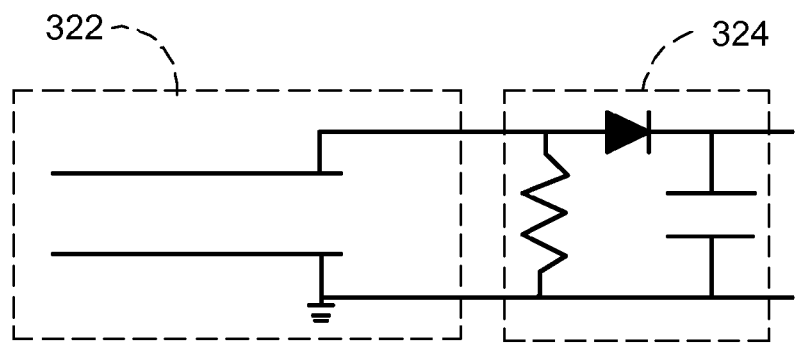
FIG. 4B is an electrical schematic of the sensing element of FIG. 4A and an electrical schematic of a transducer according to one embodiment of the present invention.

Reference is now made to FIG. 4B where there is shown an electrical schematic of a capacitive sensing element 322 such as the sensing element shown in FIG. 4A. Capacitive sensing element 322 is shown connected with a transducer 324, also presented as an electrical schematic. Transducer 324 shows an example of a diode transducer according to one embodiment of the present invention. FIG. 4B shows transducer 324 having a resistive load, a diode, and a capacitor. Preferred embodiments of the present invention minimize perturbations of the plasma produced by the impedance of the sensing element by incorporating a known resistance between the conductive electrode and base 320; this is a valuable feature for some embodiments of the present invention. The magnitude of the resistance of the parallel resistance is selected to provide both minimal perturbation of the plasma and to scale the voltages generated on the capacitor into values compatible with the measurement circuit. Resistance values between 10 ohms and 1000 ohms would be used with sensors of the dimensions given above.

Consistent and reproducible operation of the capacitive sensor is improved by having a low impedance connection to the base. This low impedance connection may be produced by either a direct (ohmic) contact between base 320 and conductive electrode 304 formed opposite conductive electrode 300 or a capacitive connection formed through the use of a very thin dielectric material. An ohmic contact may be formed through the use of a soldered or conductive adhesive connection to the base. A capacitive connection could be formed by insuring that only a thin (<5 micrometers), stable gap exists between the base and a conductive layer formed opposite the electrode.

Numerous specific combinations of electrode areas, shapes, and materials could be used to provide acceptable measurements. Similarly, there is a wide range of dielectric materials, thicknesses, and connection methods which could be utilized. In preferred embodiments of present invention, these variables are selected to meet one of more of the following design criteria: Minimize the perturbation of the plasma state in the proximity of the sensor. Provide a signal amplitude compatible with the measurement circuitry. Permit fabrication using materials and processes which both produce a stable, reproducible structure and are compatible with semiconductor device manufacturing cleanliness standards.

Furthermore, it is understood that a capacitive element such as that described in FIG. 4A and FIG. 4B is by nature sensitive to RF (displacement) currents perpendicular to the surface of the electrodes of a capacitor such as that formed by conductive electrode 300 and conductive electrode 304. Also, it is understood that a capacitive element such as that described in FIG. 4A and FIG. 4B is by nature sensitive to RF electric fields perpendicular to the surface of the electrodes of the capacitor.

Figure 4C:
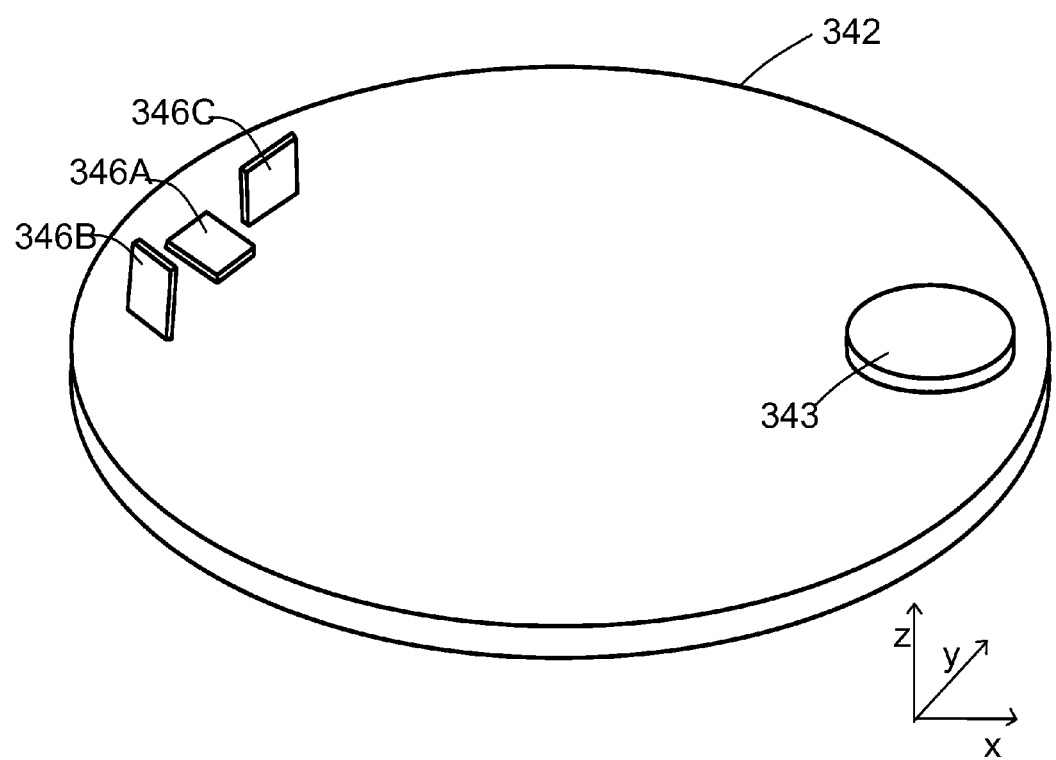
FIG. 4C is a perspective view of a sensor apparatus according to one embodiment of the present invention.

Another embodiment of the present invention is a sensor apparatus for measuring one or more direction dependent electrical properties of a plasma process for processing a workpiece. Reference is now made to FIG. 4C where there is shown a sensor apparatus for measuring one or more properties of a plasma for two or more directions. FIG. 4C shows a perspective view, primarily, of the top surface of the sensor apparatus. The sensor apparatus comprises a base 342, an information processor 343 supported on or in base 342, and a plurality of capacitive sensors supported on or in base 342 and coupled to information processor 343. The sensors have one or more capacitive sensing elements configured so as to provide an output that represents a plasma process parameter measurement. Capacitive sensing elements 346A, 346B, and 346C for a group of three capacitive sensors are oriented so that they each lie in a plane that is substantially perpendicular to the planes for each of the other capacitive sensor elements. In addition, capacitive sensing element 346A is oriented so that it lies in a plane that is substantially parallel to the surface of base 342. As an option, embodiments of the present invention include two or more groups of three sensors. Other embodiments of the present invention may be arranged so that there are only two sensors in a group and only two sensing elements in the group are oriented perpendicular to each other.

In a preferred arrangement for an embodiment of the present invention, configured for measuring a plasma property such as electric fields, the capacitive sensors or at least the sensing elements are fabricated and mounted on or in the base in various orientations so that electric fields with directions other than perpendicular to the surface of the base can be measured. Similarly, for embodiments of the present invention configured for measuring currents using capacitive sensors, the capacitive sensors or at least the sensing elements are mounted in various orientations so that currents with directions other than perpendicular to the surface of the substrate can also be measured.

As an option for some embodiments of the present invention, techniques such as those used for microelectromechanical systems, surface mount, and hybrid assembly can be used to fabricate groups of three capacitive sensors in close proximity to each other. Preferably, one of the capacitive sensors in the group is arranged so that it is substantially co-planar to the surface of the base and the capacitive sensors in each group is arranged so that it is perpendicular to the other two capacitive sensors in the group so that plasma properties such as electric fields and currents in any direction can be captured and analyzed through their x, y, and z components.

Inductive Sensing Element

Figure 5A:
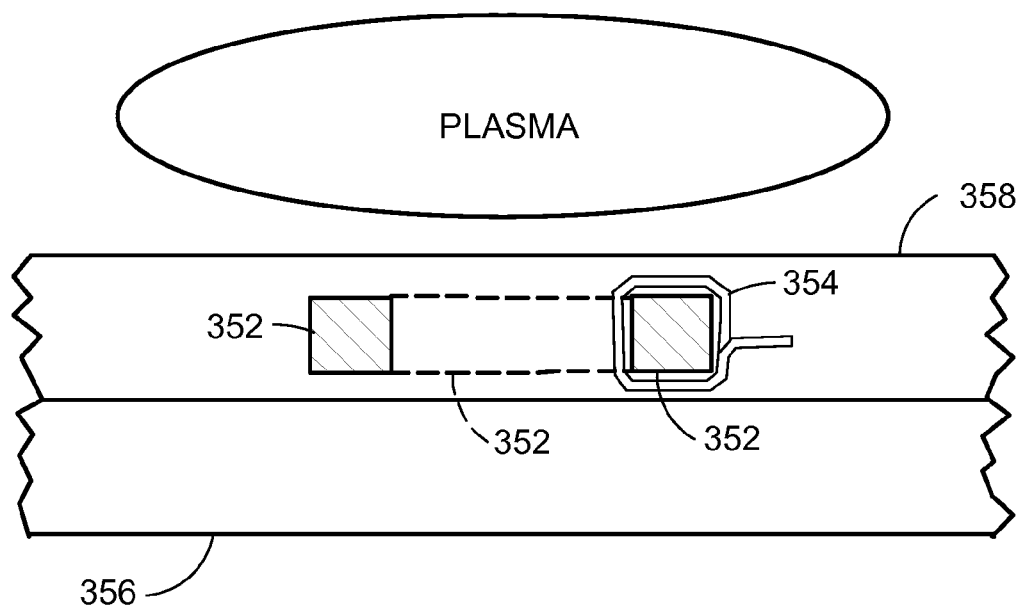
FIG. 5A is a side view of a sensing element according to one embodiment of the present invention.

Reference is now made to FIG. 5A where there is shown a cross-section side view of an example configuration of an inductive sensing element, according to the present invention. The inductive sensing element includes a ring 352 or loop made of a material with a high magnetic permeability. Ring 352 is shown in cross section in FIG. 5A. The dimensions of ring 352, as represented by enclosed area and cross section, are selected such that RF currents passing through ring 352 induce a magnetic flux within ring 352. In other words, one embodiment of the present invention includes an inductive sensing element having an induction coil with a core comprising a closed ring of magnetically permeable material enclosing an area between 0.1 cm$^2$ and 10 cm$^2$. Preferred enclosed areas between 0.1 cm$^2$ and 5 cm$^2$ provide generally acceptable performance. The ring material typically utilizes ferromagnetic elements such as iron and nickel or their alloys. These magnetic materials may be used in either metallic wire or foil form or as oxides in a ferrite composition.

The inductive sensing element also includes an electrically conductive sense coil 354 forming at least one loop enclosing the magnetic flux of ring 352 in a toroidal fashion. Magnetic flux variations induced in the inductive ring induce current flow within sense coil 354. This current is then monitored as an indicator of the RF current flow through the area enclosed by ring 352. FIG. 5A also shows base 356 supporting ring 352 and a coating of a dielectric 358 substantially covering ring 352.

Figure 5B:
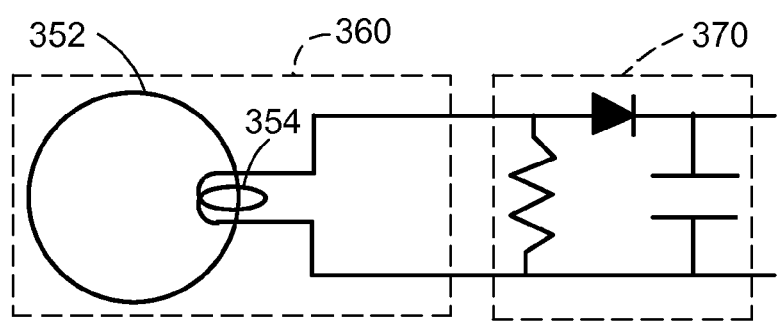
FIG. 5B is an electrical schematic of the sensing element of FIG. 5A and an electrical schematic of a transducer according to one embodiment of the present invention.

Reference is now made to FIG. 5B where there is shown an electrical schematic of an inductive sensing element 360, such as that shown in FIG. 5A, and a transducer 370 according to an embodiment of the present invention. Transducer 370 comprises a diode transducer. FIG. 5B shows ring 352 and sense coil 354. A preferred embodiment of the inductive sensor also includes a resistive load element allowing currents induced within the sense coil to produce a measurable voltage. The enclosed area of the ring, the number of turns in the sense coils, and the value of the load resistance are selected to produce a voltage compatible with the measuring circuitry. FIG. 5B shows transducer 370 having a resistive load, a diode, and a capacitor.

An inductive element is by nature sensitive to magnetic RF fields that are perpendicular to the area of the electrical loops of the coil. Thus, the example depicted in FIG. 5A is sensitive to magnetic RF fields that are co-planar to the plane of the coil which is parallel to the surface of the base. Another embodiment of the present invention comprises a sensor apparatus arranged so as to monitor such fields with directions other than parallel to the surface of the base. More specifically, an embodiment of the present invention includes inductive sensing elements fabricated and mounted in various orientations on or in the base.

Figure 5C:
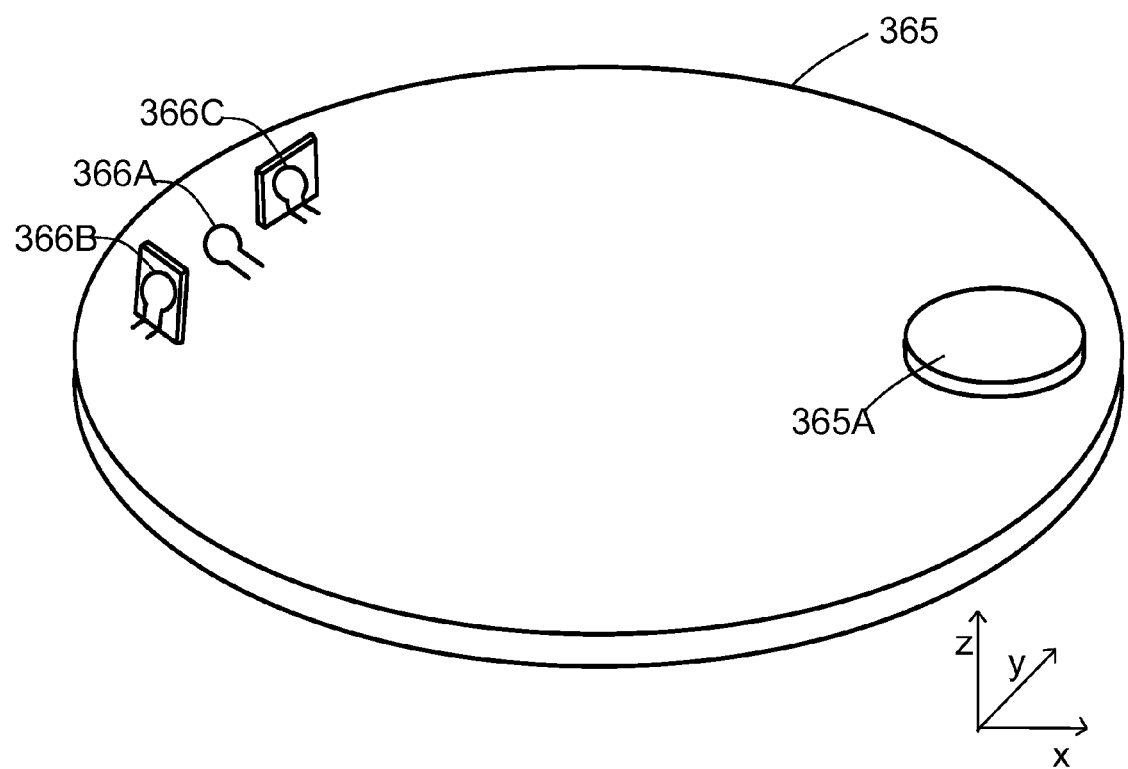
FIG. 5C is a perspective view of a sensor apparatus according to one embodiment of the present invention.

Reference is now made to FIG. 5C where there is shown a sensor apparatus for measuring one or more properties of a plasma for two or more directions. FIG. 5C shows a perspective view, primarily, of the top surface of the sensor apparatus. The sensor apparatus comprises a base 365, an information processor 365A supported on or in base 365, and a plurality of inductive sensors supported on or in base 365 and coupled to information processor 365A. The sensors have one or more inductive sensing elements configured so as to provide an output that represents a plasma process parameter measurement. Inductive sensing elements 366A, 366B, and 366C for a group of three inductive sensors are oriented so that they lie in a plane that is substantially perpendicular to the planes for each of the other inductive sensor elements. In addition, inductive sensing element 366A is oriented so that it lies in a plane that is substantially parallel to the surface of base 365. As an option, preferred embodiments of the present invention include two or more groups of three sensors. Other embodiments of the present invention may be arranged so that there are only two sensors in a group and only two sensing elements in the group are oriented perpendicular to each other.

As an option for some embodiments of the present invention, techniques such as those used for microelectromechanical systems, surface mount, and hybrid assembly can be used to fabricate groups of three inductive sensors in close proximity to each other. Preferably, one of the inductive sensors in the group is arranged so that it is substantially co-planar to the surface of the base. The inductive sensors in each group are arranged so that the sensing element of each sensor is perpendicular to the other two inductive sensor elements in the group so that plasma properties in any direction can be captured and analyzed through their x, y, and z components.

A preferred embodiment of the present invention includes a base, an information processor, and inductive sensors comprising planar coils. A benefit of using planar coils, rather than toroidal coils, is an increased simplicity of fabrication. A specific application of interest for some of the embodiments of the present invention involves the use of planar coils arranged so that they are substantially co-planar to the surface of the substrate and configured so as to detect magnetic RF field components perpendicular to the surface of the substrate. Such field components are typically associated with undesirable plasma non-uniformities and fringing field effects. In another embodiment, the planar coils are not coplanar to the surface of the base but the planar coils lie in a plane that is substantially parallel to the surface of the base.

There are numerous specific combinations of enclosed areas, shapes, and materials which could be used to provide an acceptable measurement. Similarly there is a wide range of conductive coil materials, thicknesses and numbers or turns which could be utilized. In preferred embodiments of present invention, these variables are selected to meet one of more of the following design criteria: Minimize the perturbation of the plasma state in the proximity of the sensor. Provide signal amplitudes compatible with the measurement circuitry. And, permit fabrication using materials and processes which both produce a stable, reproducible structure and are compatible with semiconductor device manufacturing cleanliness standards.

Electrostatic Charge Sensing Element

An example configuration of an electrostatic charge sensing element, according to the present invention, includes a material or structure which undergoes a measurable change in the presence of an applied electrical field such as a voltage gradient. Examples of suitable materials are semiconductors wherein the applied field can cause the movement of mobile charges within the material leading to changes in apparent resistance. One example of a suitable sensing element comprises a flexible plate structure wherein the applied field can produce deflection of the flexible plate.

Figure 6A:
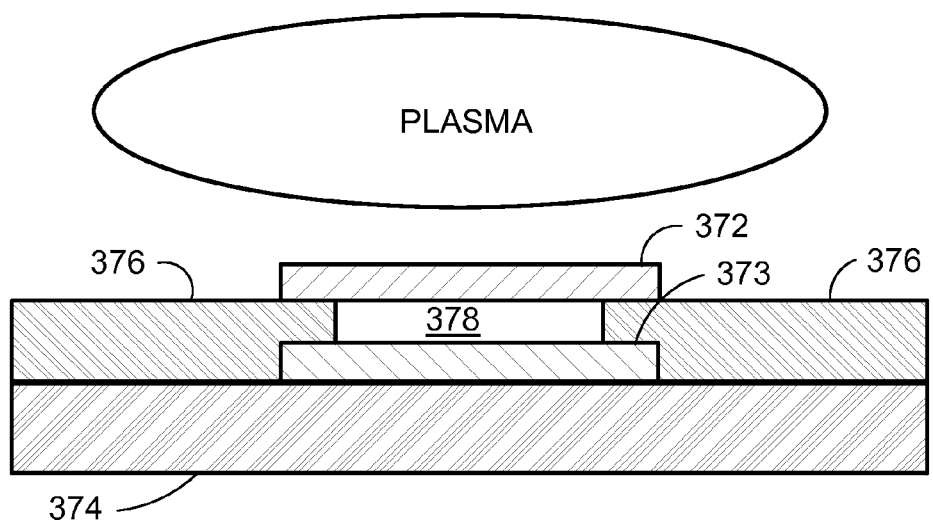
FIG. 6A is a side view of a sensing element according to one embodiment of the present invention.

Reference is now made to FIG. 6A where there is shown a cross-section side view of an electrostatic charge sensing element according to one embodiment of the present invention. FIG. 6A also shows a plasma. The charge sensing element is placed so as to measure one or more plasma parameters. The electrostatic charge sensing element includes a flexible electrical conductor 372, an electrical conductor 373, a base 374, and a dielectric 376. Electrical conductor 373 is fixedly attached to base 374. Electrical conductor 372 is suspended substantially opposite electrical conductor 374 with a portion of dielectric 376 so as to form a void 378 between electrical conductor 372 and electrical conductor 373. In this configuration, an electrical potential applied between electrical conductor 372 and electrical conductor 373 will cause electrical conductor 372 to deflect with respect to electrical conductor 373. The deflection of electric conductor 372 will cause a measurable change in the capacitance between electrical conductor 372 and electrical conductor 373. Optionally, electrical conductor 372 may comprise a metal sheet, a metal plate, or a metal film that is sufficiently flexible to produce a deflection in response to an applied field. Electrical conductor 373 may comprise a metal sheet, a metal plate, or a metal film.

Figure 6B:
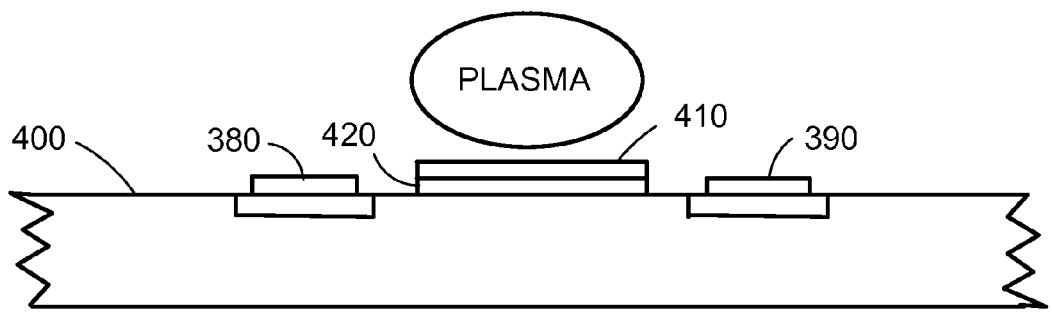
FIG. 6B is a side view of a sensing element according to one embodiment of the present invention.

Reference is now made to FIG. 6B where there is shown an electrostatic charge sensing element according to another embodiment of the present invention, the sensing element includes two electrical contacts 380 and 390 spaced apart on a lightly doped semiconductor substrate 400. In the area between the two electrical contacts, an isolated conductive plate 410 is positioned over a dielectric insulating layer 420. A voltage or potential appearing on conductive plate 410 will induce depletion or inversion in the underlying semiconductor substrate 400, causing measurable changes in the apparent resistance of this layer. A variety of materials and construction methods can be used to produce acceptable results.

Some embodiments of the present invention do not required the use of conductive plate 410. A plasma can induce a charge on the surface of insulating layer 420 which would also be effective in moderating the conductivity of semiconductor substrate 400.

Next, examples of preferred methods for fabricating examples of transducers and examples of preferred transducer configurations for embodiments of the present invention will be presented.

Diode Rectification Transducer

One embodiment of the present invention includes a sensor apparatus, as described above, comprising a transducer having a diode rectification circuit such as the diode rectification circuit shown for transducer 324 in FIG. 4B and such as the diode rectification circuit shown for transducer 370 in FIG. 5B.

Figure 7:
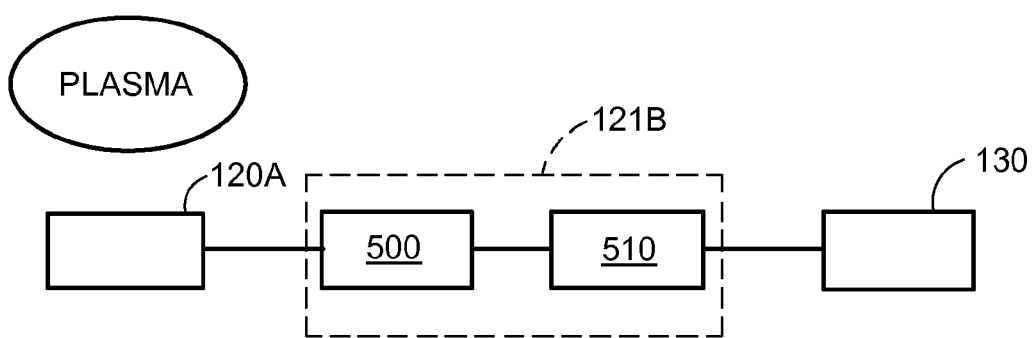
FIG. 7 is a diagram of one embodiment of the present invention.

Reference is now made to FIG. 7 where there is shown a diagram of a configuration for a transducer 121B coupled between a sensing element 120A and an information processor 130. A transducer 121B comprises a diode rectification circuit that includes a semiconducting junction diode 500 configured for rectifying an applied AC (RF) voltage or AC (RF) current from sensing element 120A so as to produce a rectified voltage or current. Transducer 121B further includes a simple low pass filter 510. The rectified voltage or current is passed through the simple low pass filter (e.g. RC) to produce a DC voltage or current proportional to the applied RF voltage. This type of transducer is compatible with a variety of sensing elements such as capacitive sensing elements and such as inductive sensing elements which provide a current output proportional to the process parameter being measured. The appropriate selection of the low pass filtering components can control both the apparent impedance of the sensor (e.g. minimize perturbation of the local plasma state) and scale the amplitude of the converted signal to be compatible with the measuring circuitry of the information processor. Another embodiment of the present invention uses capacitive coupling of the diode rectification circuit to the sensing element to eliminate potentially damaging DC current paths or to isolate the measuring circuitry from excessive voltages.

Power Detection Transducer

Figure 8:
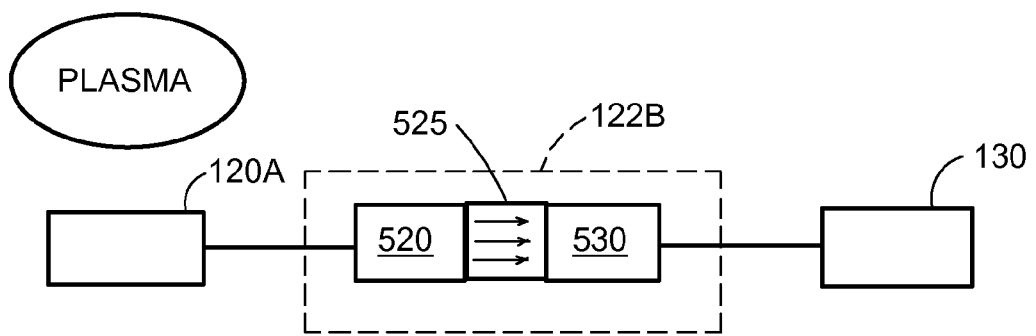
FIG. 8 is a diagram of one embodiment of the present invention.

Another embodiment of the present invention includes a sensor apparatus, as described above, comprising a transducer having a power detection circuit. Reference is now made to FIG. 8 where there is shown a diagram of a configuration for a transducer 122B coupled between a sensing element 120A and an information processor 130. Transducer 122B comprises a power detection circuit that includes a resistive load 520 such as a resistor and a temperature measuring device 530 such as a thermocouple and such as a thermistor or another type thermometer. Resistive load 520 and temperature measuring device 530 are configured so that the temperature of resistive load 520 is measured by temperature measuring device 530.

In one embodiment, resistive load 520 and temperature measuring device 530 are arranged such as would occur for temperature measurements resulting from temperature measuring device 530 physically contacting resistive load 520 for temperature measurement by thermal conduction. It is to be understood that other configurations are possible; for example, temperature measuring device 530 may be configured for measuring temperature using thermal radiation. FIG. 8 shows a more preferred embodiment where transducer 122B further includes a thermally conductive electrical insulator 525 placed between load 520 and temperature measuring device 530 so that heat flux from load 520 (as indicated by the arrows in FIG. 8) passes through the insulator to reach temperature measuring device 530.

The power detection circuit couples power captured by sensing element 120A into resistive load 520. The power dissipated within resistive load 520 results in a temperature increase in resistive load 520. This type of transducer is used in preferred embodiments of the present invention for measuring radio frequency energy and fields because the operation of the transducer is relatively frequency independent.

The measurement of the temperature can be done using components which are electrically isolated from the sensing element. This configuration can provide a more robust and noise tolerant measurement than transducer types requiring a direct (or capacitive) electrical connection to the sensing element. A preferred embodiment of the present invention includes a resistive load 520 having a resistance between 10 ohms and 1,000 ohms a thermal sensor 530 having a resistance between 10,000 ohms and 5,000,000 ohms.

Optical Transducer

Figure 9:
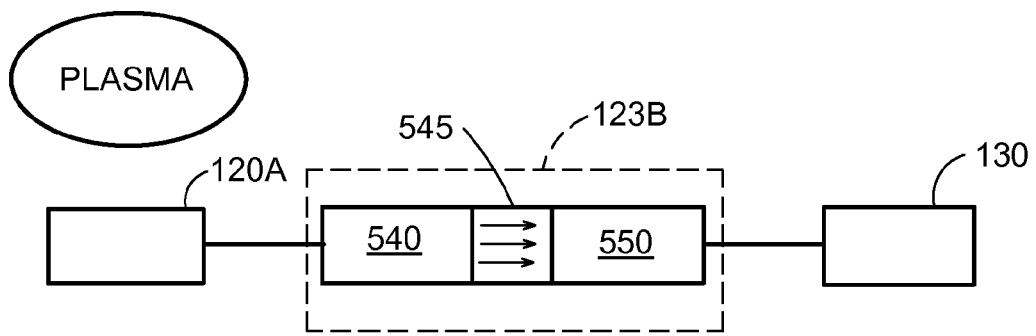
FIG. 9 is a diagram of one embodiment of the present invention.

Another embodiment of the present invention includes a sensor apparatus, as described above, comprising a transducer having an optical transduction circuit. Reference is now made to FIG. 9 where there is shown a transducer 123B coupled between a sensing element 120A and an information processor 130. Transducer 123B comprises an optical transduction circuit that includes a light emitting device 540 such as a light emitting diode and a light detecting device 550 such as a photoresistor or a photodiode. Light emitting device 540 is configured so that the intensity of the light emitted by light emitting device 540 is proportional to the current received by light emitting device 540. Light detecting device 550 is arranged so as to be capable of measuring light emitted by light emitting device 540 so as to produce a current proportional to the light produced by light emitting device 540. Transducer 123B is configured so as to allow coupling a current from sensing element 120A to light emitting device 540. Transducer 123B can be configured so as to provide electrical isolation from the plasma.

In a more preferred embodiment, transducer 123B further includes an optically transparent electrical insulator 545 placed between light emitting device 540 and light detecting device 550 so that optical emissions (shown as arrows in FIG. 9) from light emitting device 540 pass through insulator 545 to reach light detecting device 550. For some embodiments of the present invention, the optical transducer allows the optical signal to be transmitted to the measurement circuitry via fiber optic channels. In other words, some embodiments of the present invention have insulator 545 comprising optical fibers. Using the fiber optic channels, signal noise may be reduced.

Another embodiment of the present invention includes a method of operating and maintaining a process tool for processing workpieces for which the process uses a plasma. The method comprises the steps of: Providing a process tool having a robot for transferring a workpiece from a storage container or storage chamber to a workpiece holder. Providing a sensor apparatus configured for measuring one or more plasma parameters. The sensor apparatus has dimensions and physical properties that are substantially equal to the dimensions and physical properties of the workpiece. Using the robot to transfer a workpiece from the storage container to the holder for performing the process and unloading the workpiece from the holder back to the storage container. Using the robot to transfer the sensor apparatus to the holder for performing the process. Using the sensor apparatus to measure the at least one plasma characteristic during the process, and unloading the sensor apparatus from the holder using the robot.

The disclosed method and apparatus enables rapid and cost effective assessments of processing conditions within plasma processing environments such as those utilized in the manufacture of products such as integrated circuits and flat panel displays. The ability to directly monitor the plasma state, in conjunction with appropriate system models, allows the plasma process parameters to be adjusted so as to achieve optimal process performance.

Use of a sensor apparatus such as those described supra configured for data acquisition, data storage, and data communications technology allows accurate, highly resolved measurements to be made on substantially unmodified process systems running typical process recipes. Unlike embodiments of the present invention, the standard technology methods of acquiring similar data require modification of the process chamber and often require alteration of the process conditions. In addition, the use of a sensor apparatus according to embodiments of the present invention that is configured so as to be isolated from a plasma environment by an inert, transparent shield minimizes the possibility of contaminating the processing system.

One embodiment of the present invention includes a method of deploying multiple sensing elements responsive to a plasma process parameter within a plasma-processing environment. An apparatus according to one embodiment of the present invention comprises capacitive sensing elements, inductive sensing elements, electrostatic charge sensing elements, or optical emission sensing elements arrayed upon a base that can be deployed into the process system utilizing standard robotic loading capabilities of the process system. The measurement of local plasma parameter distributions are used to infer the state of the plasma and compare the inferred state based on the measurements to a reference state(s) such as past states of the plasma. Differences between the inferred current state and reference state(s) can be used to adjust plasma parameters so as to optimize the system. This data may then be used for a variety of purposes such as process optimization, process monitoring, and fault detection/identification.

Embodiments of the present invention may include sensors other than those presented above. One embodiment of the present invention includes a sensor apparatus for measuring a plasma process parameter for processing a workpiece. The sensor apparatus comprises a base and an information processor supported on or in the base. The apparatus further includes an optical sensor supported on or in the base and coupled to the information processor. The sensor has an optical sensing element configured for measuring an optical property of the plasma related to an electrical property of the plasma and a transducer coupled to the sensing element, wherein the transducer is selected from the group consisting of a diode transducer, a power transducer, and an optical transducer.

Another embodiment of the present invention is a sensor apparatus for measuring one or more plasma process parameters for processing a workpiece. The sensor apparatus comprises a base, an information processor supported on or in the base, and a plurality of sensors supported on or in the base. A preferred embodiment includes a capacitive sensor, an inductive sensor, and an electrostatic charge sensor. The capacitive sensor, inductive sensor, and the electrostatic charge sensor further comprise a transducer selected from the group consisting of: (A) a diode rectification transducer comprising a semiconductor junction diode for rectifying an applied radio frequency voltage or current and a low pass filter so as to produce a DC voltage or current proportional to the applied RF voltage or current; (B) a power transducer comprising a resistive load having a resistance between 1 ohm and 1000000 ohms and a thermistor or a thermocouple disposed so as to measure the temperature of the resistive load; and (C) an optical transducer comprising a light emitting device configured so as to provide light emissions proportional to a signal from the sensing element and an optical detector configured so as to measure the light emissions from the light emitting device.

In preferred embodiments of the present invention, the sensor apparatus is configured so as to have a thin form factor. In other words, the sensor apparatus has a thickness that approaches that for the workpiece. The design of the sensor apparatus is selected so as to have the sensor apparatus cause minimum perturbation of the plasma process during the measurements. For the most ideal design, this means having a thickness as near as possible to that of the thickness of a silicon wafer or the thickness of a flat panel display substrate or the thickness of a lithography mask substrate.

It is to be understood that the construction method and the style used to integrate and encapsulate the system components may be further modified to yield a substantially thinner sensor apparatus, perhaps even approximating the thickness of a silicon wafer used for device fabrication. An embodiment of such a sensor apparatus could be accomplished with the incorporation of MEMS integrated cavities and optical radiation sensors combined with hybrid electronic packaging.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims.

As used herein, the terms "comprises," "comprising," "includes," "including," "has," "having," "at least one of," or any other variation thereof, are intended to cover a non-exclusive inclusion. For example, a process, method, article, or apparatus that comprises a list of elements is not necessarily limited only to those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Further, unless expressly stated to the contrary, "at least one of" is to be interpreted to mean "one or more." For example, a process, method, article, or apparatus that comprises one or more of a list of elements and if one or more of the elements comprises a sub-list of sub-elements, then the sub-elements are to be considered in the same manner as the elements. For example, at least one of A and B is satisfied by any one of the following: A is true (or present) and B is false (or not present), A is false (or not present) and B is true (or present), and both A and B are true (or present).

Furthermore, a process, method, article, or apparatus that comprises one or more of a list of elements and if one or more of the elements comprises a sub-list of sub-elements, then the "at least one" is to be interpreted to mean "one or more" of the elements and sub-elements where the elements and sub-elements are to be considered part of one group of equal members. For example, at least one of A and B, where A is a list of sub-elements a1, a2, and a3, is satisfied by any one of the following: any sub-element of A is true (or present) and B is false (or not present), any of or all of the sub-element(s) of A is false (or not present) and B is true (or present), and both any sub-element of A and B are true (or present). For example, at least one of A and B, where A is a list of sub-elements a1, a2, and a3 and B is a list of sub-elements b1, b2, and b3, is satisfied by any one of the following: any sub-element of A is true (or present) and any sub-element of B is false (or not present), any sub-element of A is false (or not present) and any sub-element of B is true (or present), and both any sub-element of A and any sub-element of B are true (or present).

What is claimed is:

1. A sensor apparatus for measuring a plasma process parameter for processing a workpiece, the sensor apparatus comprising:
   a base;
   an information processor supported by the base; and
   a sensor supported by the base, the sensor comprising a sensing element configured for measuring an electrical property of a plasma and a transducer coupled to the sensing element, wherein the transducer is selected from a group consisting of:
   a) a transducer configured so as to receive a signal from the sensing element and convert the signal into a second signal for input to the information processor,
   b) a power transducer having a resistive load for receiving a current and a voltage from the sensing element and a thermometer arranged so as to measure changes in temperature of the resistive load, and
   c) an optical transducer configured so as to receive a signal from the sensing element and convert the signal into a second signal for input to the information processor, wherein the optical transducer is configured to convert an electrical signal from the sensor element to a light output and a light sensor configured to produce the second signal in proportion to an intensity of the light output that falls on the light sensor.

2. The sensor apparatus of claim 1, wherein the transducer comprises a diode rectification circuit comprising a semiconductor junction diode for rectifying an applied radio frequency voltage or current and a low pass filter so as to produce a DC voltage or current proportional to the applied RF voltage or current.

3. The sensor apparatus of claim 1 wherein the sensor includes
   a capacitive sensor supported on or in by the base and coupled to the information processor, the sensor having a capacitive sensing element configured so as to provide an output that represents a plasma process parameter measurement,
   an inductive sensor supported by the base and coupled to the information processor, the sensor having an inductive sensing element configured so as to provide an output that represents a plasma process parameter measurement, and
   an electrostatic charge sensor supported by the base and coupled to the information processor, the sensor having an electrostatic charge sensing element configured so as to provide an output that represents a plasma process parameter measurement,
   wherein the capacitive sensor, inductive sensor, or electrostatic sensor further comprise a a diode rectification transducer comprising a semiconductor junction diode for rectifying an applied radio frequency voltage or current and a low pass filter so as to produce a DC voltage or current proportional to the applied RF voltage or current.

4. The sensor apparatus of claim 2, wherein, in the diode rectification circuit, radio frequency voltages or radio frequency current induced in a capacitive or inductive sensing element are connected through the diode to a high impedance load to provide a measure of the peak to peak radio frequency potential.

5. The sensor apparatus of claim 4, wherein the radio frequency voltages or radio frequency current are induced in a capacitive or an inductive sensing element and the capacitive or inductive sensing element is connected to a low impedance load to provide a measure of the local radio frequency current.

6. The sensor apparatus of claim 4, wherein identical sensor elements are connected to impedances of different values so as to be capable of measuring nonlinear plasma current-voltage characteristics.

7. The sensor apparatus of claim 4, wherein a signal from the sensing element is applied to a complex load having resistive, inductive, and capacitive properties so as to be capable of making frequency sensitive measurements.

* * * * *